(12) United States Patent
Persson et al.

(10) Patent No.: US 11,963,765 B2
(45) Date of Patent: Apr. 23, 2024

(54) SYSTEM AND METHOD FOR RAPID BLOOD GAS MONITORING

(71) Applicant: Fourth State Systems AB, Uppsala (SE)

(72) Inventors: Anders Persson, Bälinge (SE); Martin Berglund, Uppsala (SE)

(73) Assignee: Fourth State Systems AB, Uppsala (SE)

( * ) Notice: Subject to any disclaimer, the term of this patent is extended or adjusted under 35 U.S.C. 154(b) by 26 days.

(21) Appl. No.: 17/251,976

(22) PCT Filed: Jun. 1, 2020

(86) PCT No.: PCT/SE2020/050551
§ 371 (c)(1),
(2) Date: Dec. 14, 2020

(87) PCT Pub. No.: WO2021/006786
PCT Pub. Date: Jan. 14, 2021

(65) Prior Publication Data
US 2022/0117526 A1    Apr. 21, 2022

(30) Foreign Application Priority Data
Jul. 5, 2019  (SE) .................................. 1950857-1

(51) Int. Cl.
*A61B 5/145* (2006.01)
*A61B 5/00* (2006.01)
(Continued)

(52) U.S. Cl.
CPC ........ *A61B 5/14552* (2013.01); *A61B 5/1491* (2013.01); *A61B 5/742* (2013.01); *H05H 1/46* (2013.01)

(58) Field of Classification Search
CPC ... A61B 5/145; A61B 5/1455; A61B 5/14551; A61B 5/14552; A61B 5/742;
(Continued)

(56) References Cited

U.S. PATENT DOCUMENTS

| 4,439,679 A | 3/1984 | McIlroy et al. |
| 9,538,944 B2 | 1/2017 | Rao et al. |

(Continued)

FOREIGN PATENT DOCUMENTS

| CN | 1153463 A | 7/1997 |
| CN | 104540449 A | 4/2015 |

(Continued)

OTHER PUBLICATIONS

Fröjdholm et al., "Toward non-invasive neonatal gas monitoring with plasma-based spectroscopy", Uppsala University Thesis paper, Jun. 13, 2018, XP055724948, Retrieved from the Internet: URL:https://www.diva-portal.org/smash/get/diva2:1214200/FULLTEXT01.pdf.

(Continued)

*Primary Examiner* — Chu Chuan Liu
(74) *Attorney, Agent, or Firm* — Morgan, Lewis & Bockius LLP

(57) ABSTRACT

The present invention relates to a sampling unit, a measurement system and method for transcutaneous blood gas measurements. In particular the invention relates to a sampling unit and system adapted for rapid measuring and monitoring of blood gases in a continuous gas flow. The sampling unit is provided with an ambient air inlet and a blood gas extraction and mixing chamber wherein air is mixed with extracted blood gases. The method of continuous transcutaneous measurement of carbon dioxide in the blood utilizes a pulsed heating to minimize the detrimental effects of the heating.

19 Claims, 8 Drawing Sheets

(51) Int. Cl.
*A61B 5/1455* (2006.01)
*A61B 5/1491* (2006.01)
*H05H 1/46* (2006.01)

(58) Field of Classification Search
CPC . A61B 5/6834; A61B 5/6801; A61B 5/14542; A61B 5/1491
See application file for complete search history.

(56) References Cited

U.S. PATENT DOCUMENTS

| | | | |
|---|---|---|---|
| 9,784,712 B2 | 10/2017 | Persson et al. | |
| 10,265,006 B2 | 4/2019 | Kahlman et al. | |
| 2009/0156914 A1* | 6/2009 | O'Neil | A61B 5/083 600/314 |
| 2012/0215124 A1 | 8/2012 | Fisher et al. | |
| 2013/0281806 A1 | 10/2013 | Rao et al. | |
| 2015/0173662 A1 | 6/2015 | Ulman et al. | |
| 2016/0123927 A1 | 5/2016 | Persson et al. | |
| 2017/0196489 A1 | 7/2017 | Horras et al. | |
| 2017/0312120 A1 | 11/2017 | Kahlman | |
| 2018/0153440 A1 | 6/2018 | Lee et al. | |

FOREIGN PATENT DOCUMENTS

| | | |
|---|---|---|
| CN | 104918550 A | 9/2015 |
| CN | 105759022 A | 7/2016 |
| EP | 3050180 B1 | 12/2018 |
| WO | 94/16614 A1 | 8/1994 |
| WO | 2016/008840 A1 | 1/2016 |
| WO | 2016/173877 A1 | 11/2016 |
| WO | 2017/023500 A1 | 2/2017 |

OTHER PUBLICATIONS

Berglund et al., "Microplasma source for optogalvanic spectroscopy of nanogram samples", Journal of Applied Physics, vol. 114, No. 3, Jul. 21, 2013, p. 033302, XP055724957, US.
Bromley, "Transcutaneous monitoring—understanding the principles", Infant, vol. 4, p. 95-98, 2008.
"Transcutaneous Blood Gas Monitor", http://www.who.int/medical_devices/en/index.html, World Health Organization, Core Medical Equipment—Information Sheet 2011.
Lübbers, "Theoretical basis of the transcutaneous blood gas measurement", Critical Care Medicine, vol. 9, No. 10, pp. 721-733, 1981.
Magerl et al., "Heat-evoked vasodilatation in human hairy skin: axon reflexes due to low-level activity of nociceptive afferents", Journal of Physiology, 497.3, pp. 837-848, 1996.
International Search Report and Written Opinion dated Sep. 4, 2020, issued in corresponding International Patent Application No. PCT/SE2020/050551.
Office Action dated Sep. 28, 2023, issued in corresponding Chinese Patent Application No. 202080046868.9.

* cited by examiner

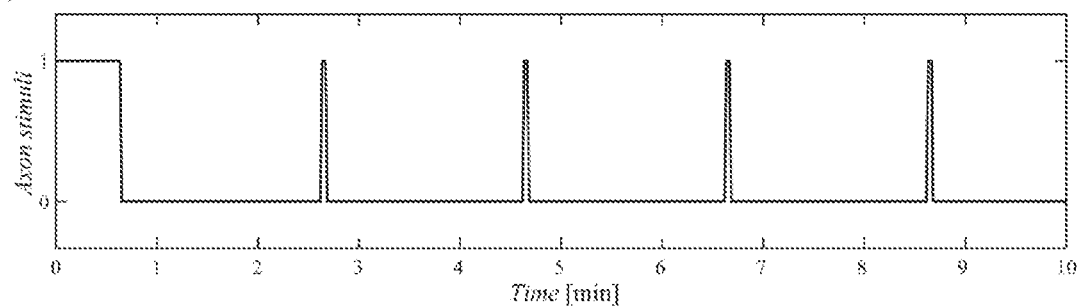
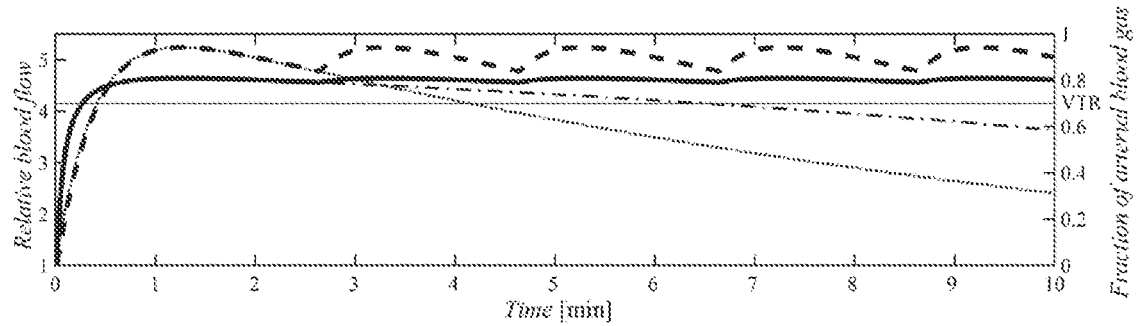
*Fig. 10a-b*

SYSTEM AND METHOD FOR RAPID BLOOD GAS MONITORING

FIELD OF INVENTION

The present invention relates to a sampling unit, a measurement system and method for transcutaneous blood gas measurements. In particular the invention relates to a sampling unit and system adapted for rapid measuring and monitoring of blood gases in a continuous gas flow and a method of continuous transcutaneous measurement of carbon dioxide in the blood of the patient wherein the skin of the patient is heated and to minimize the detrimental effects of the heating.

BACKGROUND

Transcutaneous blood gas measurements (TBM) are pivotal in monitoring the health of prematurely born children. Blood gases refer to the partial pressure of oxygen ($O_2$) and carbon dioxide ($CO_2$) in the blood of the patient, and transcutaneous means to measure through the skin. About 75% of all neonates are monitored by TBM during their hospitalization, making it one of the most widely used methods in a modern Neonatal Intensive Care Unit (NICU). [1]

Together with measurements of pulse, respiration rate, body temperature, and blood oxygen saturation, TBM forms the backbone of monitoring the basic health of a neonate, where TBM gives unique information about both respiratory and circulatory function. Many neonates, particularly those born into extreme prematurity, have organs that are far from sufficiently developed to support them outside the womb. Hence, both lungs and heart may struggle to achieve proper oxygenation, and the patient must be treated in an incubator with increased ambient $O_2$ levels. However, it is crucial to keep the added $O_2$ at a healthy level, since hyperoxia, i.e., too much oxygen in the patient's blood, may cause morbidity by damaging the central nervous system and often causes blindness by hampering the development of the optic nerve. Hypoxia, i.e. too little $O_2$, on the other hand, may cause both morbidity and even mortality from insufficient oxygenation of the brain and other vital organs.

In principle, there are three different kinds of blood gas measurements depending on in what kind of vessel the sample is taken—arterial, capillary or venous—each giving different information about the patient's health. Which ones are of interest depends on the patient's condition, but in general, the arterial $O_2$ pressure and the capillary and arterial $CO_2$ pressure are of the most interest to an NICU.

In TBM, the measurement is achieved by placing a Transcutaneous blood gas measurement system (TBM system) on the patient's skin, which collects and analyzes the minute amount of gas that diffuses from the cutaneous capillaries through the surrounding tissue and out through the skin. Current TBM systems consists of two integral parts, namely a sampling unit that collects the blood gases at the skin surface and conducts them to a sensor unit that analyses the respective gas contents. In order to keep the sampling rate at a maximum, the dead volumes in the system are minimized. Therefore the sensor unit is typically integrated inside the sampling unit. In the end, the sampling rate is primarily dependent on the transcutaneous mass transfer to reach equilibrium inside the hermetically sealed sampling unit. [2]

However, this system is not sufficient to perform TBM in a way that is relevant to neonatal health care, since the sampling rate is too low to detect important changes in the patient's health due to the minute transcutaneous gas flow. Moreover, the configuration does not allow for measurements of the arterial $O_2$ pressure. To solve both these issues, the system is equipped with a third component, namely a heater connected to a power supply that continuously heat the skin beneath the sampling unit to temperatures between 42° C. and 45° C. The elevated temperature causes the cutaneous capillaries to dilate, which greatly increases the cutaneous blood flow. The increased blood flow lets more arterial blood enter the capillaries, and, hence, the capillary $O_2$ pressure approaches arterial levels. The elevated temperature and increased access to $O_2$ also increases the metabolism in the cells beneath the sampling unit, in the same time as the solvability of $CO_2$ in the blood is reduced. Both these effects increase the transcutaneous $CO_2$ flux, hence, increasing the system's sampling rate towards one measurement every 10 minutes. [3]

The typical sampling unit of a current TBM system is a stiff plastic cup with a diameter of approximately 2 cm, which restricts the parts of a neonate's body that the system can be attached to. The system has to be attached to a flat surface of skin to avoid leakage, which generally limits attachment to the patient's, torso where it has to compete for space with other equipment such as ECG electrodes for example.

WO 2016/173877 discloses a sensor for non-invasive measurement of the partial pressure of $CO_2$ in the skin of a human. The sensor comprises a housing, a gas measuring chamber for measuring gases, at least one chimney for communication of gases diffusing through the skin to the gas measuring chamber, a broad band light source transmitting light into the gas measuring chamber and a detector system comprising a first and a second photodetector. The first photodetector detects light at a wavelength wherein $CO_2$ absorbs light and the second photodetector acts as a zero reference detector by measuring light in a freehand where no gases absorb light.

U.S. Pat. No. 9,538,944B2 discloses a non-invasive gas analyte sensing and monitoring system and method that is particularly applicable to transcutaneous monitoring of arterial blood gases in a mammal. The system and method relies on diffusion of the analyte to be measured into a diffusion chamber and remote sensing of the analyte in the diffusion chamber using optical chemical sensors and associated optoelectronics.

U.S. Pat. No. 9,784,712B2 discloses a miniaturized plasma source that includes a stripline split-ring resonator. The split-ring resonator is sandwiched between two dielectric substrates and two metal ground planes. In order to make the plasma accessible from the outside of the ground planes, a hole is made through the gap between the ends of the split ring. The two ground planes act as an electromagnetic shield, protecting the split-ring resonator from electromagnetic interference due to changes in the electric or dielectric environment surrounding it. The miniaturized plasma source is particularly useful in plasma emission and optogalvanic spectroscopy applications. U.S. Pat. No. 9,784,712B2 is hereby incorporated by reference in its entirety.

WO 2016/008840 A1 discloses to monitor the blood gases at a lower temperature with a cutaneous sensor, and intermittently warm up the skin to a temperature of 42° C. or more for a short duration to monitor the transcutaneous partial pressure of oxygen, before lowering the temperature to a lower set point. There is still a need for a TBM system with a sampling rate that is higher than every $10^{th}$ minutes. There is also a need for a TBM system that does not require continuous heating of the patient's skin or flushing with nitrogen or air that both, although for different reasons, interrupts the measurement.

SUMMARY

The object of the invention is to provide a system and method for TBM measurements that overcomes the drawbacks of the prior art. This is achieved by the sampling unit as defined in claim 1, the system as defined in claim 13 and the method as defined in the claims.

The sampling unit according to the invention is to be used in a system for transcutaneous blood gas measurement. The system comprises a sensor unit, a tube and a pump. The pump enables a gas flow into the sampling unit through the tube and to the sensor unit. The sensor unit is configured to measure the gas composition of the gas flow and the sampling unit is configured to during use be attached to the skin of a patient. The sampling unit comprises at least one ambient air inlet, and at least one blood gas extraction and mixing cavity in fluid connection with the ambient air inlet and in fluid connection with an outlet configured to be connected to the tube. The ambient air inlet is arranged to continuously provide ambient air to the blood gas extraction and mixing cavity. The blood gas extraction and mixing cavity is provided on the side of the sampling unit facing the skin.

According to one aspect of the invention the sampling unit is made in a material with a Young's modulus of less than $10^5$ kPa. The sampling unit may be made of one of the materials or a combination of: polydimethylsiloxande, silicone, capton, and rubber.

According to one aspect of the invention the combination of the outlet and the tube has a flow resistance at or less than the ambient air inlet or the combined flow resistance of a plurality of ambient air inlets. Preferably the combination of the outlet and the tube has an 1-2 times lower flow resistance than the ambient air inlet or the combined flow resistance of a plurality of ambient air inlets. According to one aspect of the invention the cross-section of the outlet and/or the internal cross-section the tube is larger than the cross-section of the ambient air inlet or the combined cross section of a plurality of ambient air inlets.

According to one aspect of the invention the tube and/or outlet has an internal cross-section of 0.0020 $mm^2$-0.031 $mm^2$, preferably 0.0028 $mm^2$-0.0079 $mm^2$.

According to one aspect of the invention the at least a portion of the sampling unit is made in a gas permeable material that serves as a blood gas extraction and mixing cavity and has one skin facing side facing the skin and one ambient air facing side in fluid connection with the ambient air. The combination of the outlet and the tube may preferably have a flow resistance at or less than that of air entering the sampling unit through ambient air facing side passing through the gas permeable material and exiting to the outlet.

According to one aspect of the invention the sampling unit comprises a nerve stimulating element configured to stimulate an axon reflex in small nerve fibers close to the skin. The nerve stimulating element may typically be a heater, for example a resistive heater.

According to one aspect of the invention the nerve stimulating element is a combined heater and ECG electrode.

The system for transcutaneous blood gas measurement according to the invention for measurement of carbon dioxide comprises a sampling unit according to one of the above described embodiments, a sensor unit, a tube connecting the sampling unit and the sensor unit, and a pump configured to enable a gas flow into and through the sampling unit, through the tube into and through the sensor unit.

According to one aspect of the invention the sensor unit comprises a microplasma source having an internal volume of at or less than 100 $mm^3$ and an operating pressure of at or less than 40 kPa.

According to one aspect of the invention the microplasma source is a stripline split-ring resonator microplasma source.

According to one aspect of the invention the sensor unit comprises several sensors to measure different gases, primarily blood gases. The sensor unit may be configured to also measure and detect the amount of other gases, for the purpose of detecting leaks, example of such gases are, but not limited to $N_2$ and/or Ar in the gas coming from the sampling unit.

According to one aspect of the invention the sensor unit is a two-tube sensor unit, that is connected to the sampling unit with two tubes, wherein the first tube is connected to the outlet, and the second is collecting ambient air from a place close to sampling unit but away from the patient skin. The two-tube sensor unit may be configured to toggle between the two tube inputs.

It is an advantage with the invention that the sampling rate is higher than every 10th minute. This is not only time saving but it also makes it possible to detect acute events like apneas and circulatory failures.

It is an advantage with the invention that the concentration gradient across the skin is stabilized which enables a stable transcutaneous gas flux.

It is an advantage with the invention that the sampling unit is made in a soft material and therefore can be attached to more uneven or curved locations at the patient's skin, and not only the torso.

It is a further advantage with the invention that the soft sampling cup does not need to be glued to the patient's skin in order to avoid gas leaks. Hence, it can be removed without the risk of tearing the patient's skin if needed.

It is an advantage with the invention that an increased transcutaneous gas flux may be obtained which improves the resolution and reduces the response time of the sensor unit.

It is an advantage that the atmospheric gases can be used to continuously calibrate the system and, hence, improve both the accuracy and the stability of the measurement.

It is an advantage with the invention the system can detect gas leaks and differentiate such from health emergencies. This is specially advantages at an NICU where the patients are in need of a calm and silent environment.

It is an advantage with the invention that it does not require the use of adhesive and thus is possible to use for extremely premature children whose skin is not mature enough to handle adhesives.

It is an advantage with the invention that it does not require continuous heating of the patient's skin and therefore limit the risk for skin burns.

It is a further advantage with the invention that when there is no continuous heating the system does not need to be continuously relocated on the patient, something that is both time and labour intensive and also causes a pause in the measurement after which the system has to be recalibrated. The full procedure takes roughly 20-30 minutes. Hence, systems of the invention save both time and labour and enable uninterrupted measurement.

It is an advantage with the invention that it offers the possibility to measure both the capillary and arterial blood gas values with a sampling rate higher than every 10th minute. It may also offer the possibility of switching between the different measurement methods without changing or dethatching the system. Capillary and arterial values contribute with unique and independent information about the patient's health status. Capillary values offer local information about the status of the body close to the measurements site. Arterial values, on the other hand, offers information of the status of the body as a whole. Hence, by switching between arterial and capillary monitoring, it is possible to deduce much more information about the health of the patient than by monitoring one of these values alone.

It is an advantage with the invention that ECG measurement and TBM measurements can be integrated into a single sampling site on the patient's skin. Such combined use constitutes a great practical advantage, since neonates generally have to be monitored by up to five different instruments: TBM, ECG, pulse oximetry, respiration and temperature. Moreover, at least the instruments for measuring TMB, ECG, and respiration should be attached to the limited space on the neonate's torso.

One advantage afforded by the use of a gas permeable material in the sampling unit is that the sampling unit is inexpensive and easy to manufacture.

The method for continuous transcutaneous blood gas monitoring according to the invention utilizes a sampling unit placed on the skin of a person, the transcutaneous blood gas monitoring system comprising a sampling unit provided with a nerve stimulating element and at least a carbon dioxide sensor. The method comprises concurrent steps of:
- continuously transmitting a continuous pulsed signal to a nerve stimulating element that transmits a continuous series of stimulation pulses to the skin of the person, thereby inducing vasodilation in the cutaneous capillaries located at the interface of the sampling unit;
- continuously extracting the transcutaneous blood gas from the patient into the transcutaneous blood gas monitoring system;
- continuously measuring the extracted transcutaneous blood gas with the transcutaneous blood gas sensor; and
- continuously analyzing the signals from the carbon dioxide sensor and determining and presenting a carbon dioxide transcutaneous blood gas value.

According to one aspect of method of the invention the step of continuously transmitting a continuous pulsed signal the continuous pulsed signal is arranged to maintain the vasodilation in the cutaneous capillaries above a predetermined vasodilation threshold value.

According to one aspect of method of the invention the step of continuously measuring the extracted transcutaneous blood gas includes continuously measuring the carbon dioxide in the extracted transcutaneous blood gas with a carbon dioxide sensor configured to measure the partial pressure of the extracted transcutaneous blood gas.

According to one aspect of method of the invention the continuous pulsed signal has a maximum power level, MPL, corresponding to a maximum temperature of the skin of 42-45° C. and the nerve stimulating pulses (SP) has a pulse width, PW, between 2 and 180 s and the relaxation period, RP, is between 105 and 180 s.

According to one aspect of method of the invention the continuous pulsed signal has a maximum power level, MPL, corresponding to a maximum temperature of the skin of 42-45° C. and the nerve stimulating pulses (SP) has a pulse width, PW, between 2 and 15 s and the relaxation period, RP, is between 105 and 118 s.

According to one aspect of method of the invention the continuous pulsed signal has a maximum power level, MPL, corresponding to a maximum temperature of the skin of 42-45° C. and the nerve stimulating pulses (SP) has a pulse width, PW, between 2 and 8 s and the relaxation period, RP, is between 120 and 180 s.

It is an advantage with the invention that the TBM system can remain attached to the same site for long periods of time, i.e. without having to be relocated after a few hours to avoid the formation of skin burns. Avoiding relocation saves both time and labor. This is a particular advantage for neonates since the total number of locations on the body suitable for attachment of a TBM system are more or less limited the torso where it competes for space with ECG electrodes etc.

It is a further advantage with the invention that it increases the safety for the patient. The system must be glued very tightly to the skin to avoid gas leakages. Hence, removing it from the skin risk causing tears that in turn might cause infections. Neonates are particular sensitive to infections and minimizing this risk by avoiding relocation of the TBM system will consequently improve the safety and quality of their care.

It is an advantage with the invention that the measurement can be performed continuously without the need for interruptions. A current system for TBM must either be relocated or turned off to allow the skin beneath the system to recover and not be burnt. If the system is relocated, the sensor unit needs to be recalibrated, and the whole process typically takes between 20 and 30 minutes. If the system, or its heater, is instead turned off, it needs to stay off for at least 20 minutes for the skin to recover. Both these measures cause a pause in the measurement.

It is further advantage with the method of the invention that it facilitates continuous measurement of the patient's blood gas status and hence provides the care-takers with real-time data.

It is a further advantage that the duty cycle of the continuous pulsed signal may be precisely controlled that not only lower the risk of skin burns, but also minimizes spurious signals arising from increased metabolism in the heated tissue, and, hence, offers a more precise measurement of the arterial blood gases.

DESCRIPTION OF DRAWINGS

FIG. 10 a) is a graph showing a continuous pulsed signal for axon reflex stimulation, and b) is a graph showing relative blood flow and fraction arterial gas content of cutaneous capillaries as a function of time;

DETAILED DESCRIPTION

Figure 1:
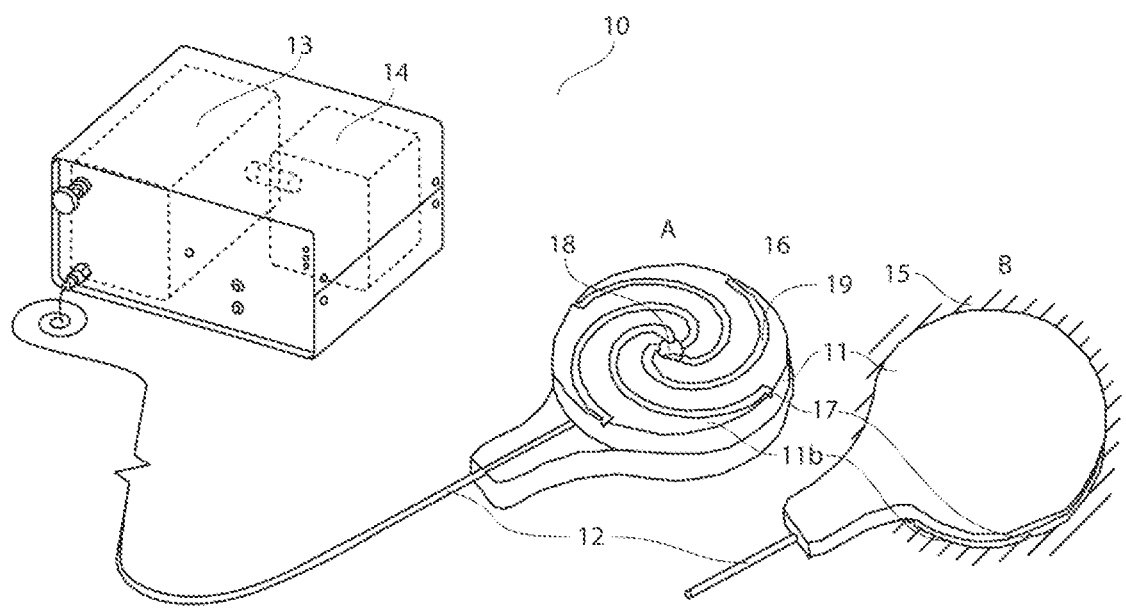
FIG. 1 is a schematic illustration of the sampling unit and TBM system according to the invention.

In the following the following terms are used:
Cutaneous—located close to the skin;
erythema—redness of the skin or skin burns;
stimulation pulse—continuous series of pulses transmitted to the small cutaneous nerve fibers;
TBM—transcutaneous blood gas measurement;
TBM system—system for transcutaneous blood gas monitoring;
transcutaneous—through the skin; and
vasodilation—widening of blood vessels' cross section.

Terms such as "top", "bottom", upper", lower", "below", "above" etc. are used merely with reference to the geometry of the embodiment of the invention shown in the drawings and/or during normal operation of the described device and system and are not intended to limit the invention in any manner. It should be noted that the figures, if not otherwise stated, does not show the systems according to any scale, external or internal.

Figure 12:
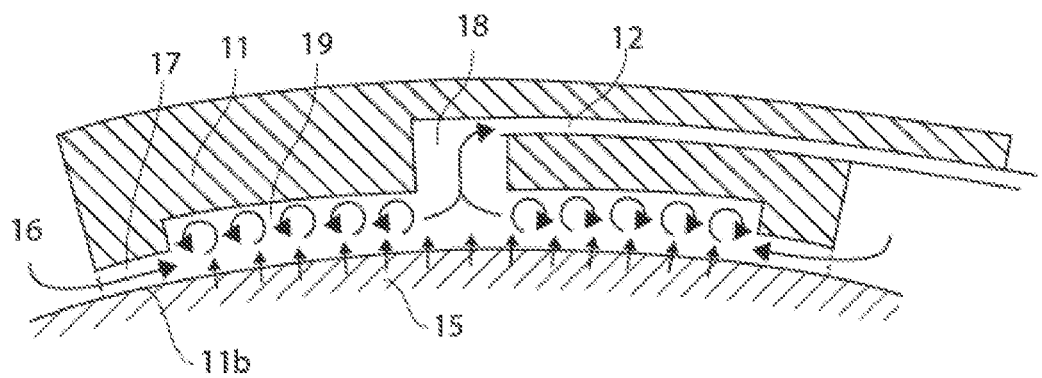
FIG. 12 is a schematic illustration of the flow and mixing of gas in a sampling unit according to the invention.

The invention relates to a transcutaneous blood gas measurement system, TBM system, including capillary and/or arterial $CO_2$ and $O_2$ measurements, based on gas flow. The TBM system 10 according to the invention, schematically illustrated in FIG. 1, comprises a sampling unit 11, a tube 12, a sensor unit 13, and a pump 14. The sampling unit 11 is configured to be attached to a patient's skin 15 in a way that $CO_2$ and $O_2$ that diffuse from the blood through the patient's skin 15 is collected by the sampling unit 11. The bottom surface 11b of the sampling unit 11 is the part facing the skin 15. The sampling unit 11 has one or more ambient air inlets 17 and a single outlet 18. At least one ambient air inlet 17 is open to ambient air 16 and the outlet 18 is connected to the sensor unit 13 via the tube 12. Between the ambient air inlet 17 and the outlet 18 is a blood gas extraction and mixing cavity 19 provided with one side facing the patient's skin 15. The walls of the blood gas extraction and mixing cavity 19 form, together with the skin 15 exposed by the cavity, a blood gas extraction and mixing chamber, wherein the ambient air from ambient air inlet 17 and the extracted blood gases mix. When the pump 14 is turned on, air flows from the ambient air inlet 17, through the blood gas extraction and mixing cavity 19, to the outlet 18, on through the tube 12 to the sensor unit 13, which has the capacity to measure the amount of $O_2$ and $CO_2$ in the gas that is transported through the tube 12. In the blood gas extraction and mixing chamber 19 formed during use by the cavity and the skin, the ambient air mixes with the blood gases. This flow-based approach stabilizes the concentration gradient across the skin and, hence, maintains a stable transcutaneous gas flux. Therefore, a TBM system of the invention that relies on gas flow may facilitate much faster sampling rates compared to a TBM system that relies on a closed volume attached to the skin to reach equilibrium by the transcutaneous gas flux. FIG. 12 is a schematic illustration of the gas flow in a sampling unit 11 according to the invention. As can be seen in FIG. 12 air from the ambient air 16 enters the sampling unit 11 at the ambient air inlet 17. The ambient air inlet 17 is continuously open to the ambient air 16 during use. The air continues into the blood gas extraction and mixing chamber 19 where it is mixed with blood gases diffusing through the skin 15 underneath the sampling unit 11. The gas mixture formed in the gas extraction and mixing chamber 19 continues via the outlet 18 to the tube 12 and finally to the sensor unit 13 (not shown in FIG. 12).

In one embodiment the cross-section of the gas extraction and mixing chamber 19 is the same size or up to 3 times the size of the cross-section of the ambient air inlet 17. In one embodiment the length of the gas extraction and mixing chamber 19 is 30-300 times longer than the length of the ambient air inlet 17. All the size estimates are in the direction of the gas flow.

The ambient air inlet 17 is according to one embodiment open to the skin 15 as depicted in FIG. 1. In this case the part of the ambient air inlet 17 facing the skin can be seen as integrated with and contributing to the blood gas extraction and mixing cavity 19. Alternatively, the ambient air inlet 17 is provided as a through-hole from the surface of the sampling unit 11 to the blood gas extraction and mixing cavity 19.

The blood gas extraction and mixing cavity 19 may for example be formed as a smooth depression in the surface of the sampling unit 11. Alternatively, the blood gas extraction and mixing cavity 19 has a side wall essentially perpendicular to the bottom surface 11b of the sampling unit 11 and a top surface essentially parallel to the bottom surface 11b of the sampling unit 11. The depth of the depression or height of the side wall of the blood gas extraction and mixing cavity 19 is typically in the order of 0.05 to 0.5 mm. The area of the opening facing the skin 15 of the blood gas extraction and mixing cavity 19 is in the order of 5 to 500 $mm^2$.

According to one embodiment the sampling unit 11 is provided with a plurality of ambient air inlets 17 and a plurality of blood gas extraction and mixing cavities 19. One or more ambient air inlets 17 are connected to one of the plurality of blood gas extraction and mixing cavities 19 and all blood gas extraction and mixing cavities 19 are connected to the common outlet 18. In an alternative embodiment all the of ambient air inlets 17 are connected to one common blood gas extraction and mixing cavity 19.

Figure 2:
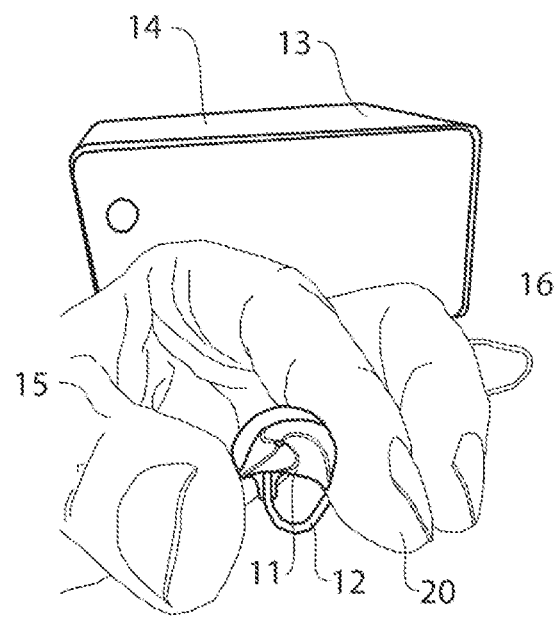
FIG. 2 is a schematic illustration of the sampling unit and TBM system according to the invention.

FIG. 2 shows an illustrative drawing of one embodiment of the invention and provides a non-binding approximate size of the sampling unit 11, being held between fingertips 20, as well as illustrating the flexibility of the sampling unit 11 according to the embodiment.

The functions of the parts of the TBM system 10 are further described with reference to FIG. 1:

The pump 14 enables gas to flow into a sampling unit 11, through a tube 12 and to a sensor unit 13. The sampling unit 11 is during use attached to the skin of a patient 15.

The sensor unit 13 measures the gas composition of the gas flow. The sensor unit may house one or more separate sensors for several different gases such as $O_2$, $CO_2$, Ar, $N_2$ etc.

The analog output of the sensor unit 13 is filtered, amplified and converted to a digital signal in an analog-to-digital converter (not shown).

The digital signal is post-processed and logged by a computer (not shown).

Gas from the ambient air 16 enters the sampling unit 11 of the TBM system 10 through the ambient air inlet 17, the ambient air inlet 17 is constantly open to the ambient air 16 during use of the TBM system 10.

When gas from the ambient air 16 flows through the sampling unit 11 along the surface of the patient's skin, it is mixed with the blood gases that are diffusing through the patient's skin 15. This gas mix is then transported to the tube 12 and to the sensor unit 13.

New gas continuously enters the sampling unit 11 from the ambient air 16 and the concentration gradient of the blood gases across the surface of the skin 15 is therefore stabilized, hence, creating a steady and continuous transcutaneous blood gas flux and avoiding the need to wait until the blood gas concentration on the surface of the patient's skin 15 reach equilibrium before a measurement can be done.

The sensor unit 13 can house one or more separate sensors. In one embodiment of the invention, the sensor unit 13 comprises a stripline split-ring resonator microplasma source such as described in U.S. Pat. No. 9,784,712B2. This microplasma source is used to measure the transcutaneous $CO_2$ and $O_2$ flux by either emission spectroscopy or by optogalvanic spectroscopy. In other embodiments of the invention, the plasma or discharge can be created with other types for microplasma sources, e.g. those relying on dielectric barrier discharges, cathode boundary layers, capillary plasma electrode discharges, inductively coupled plasma, capacitively coupled plasma, hollow cathode discharges, or radio-frequency and microwave resonators. However, in all embodiments of the invention, the internal volume of the microplasma source is less than 100 $mm^3$, and its operating pressure is less than 40 kPa.

When a microplasma source is used to perform emission spectroscopy, light from the discharge illuminates a prism or grating through a slit. The refracted or diffracted light is projected on a CCD detector, making it possible to record the emission spectrum of the discharge. The recorded spectrum can then be post processed to detect and quantify the emitting species in the discharge. When the plasma source is used to perform optogalvanic spectroscopy, the discharge is illuminated with a laser beam that is in resonance with one of the molecules in the gas. When these molecules absorb laser photons, they heat the gas, hence, affecting its impedance. The plasma impedance is measured with electrical probes protruding into the plasma and the change in impedance is directly proportional to the number of molecules of the investigated species.

In one embodiment, when a microplasma source is used to perform emission or optogalvanic spectroscopy, the sensor unit comprises several sensors that can measure any of the gases $CO_2$, $O_2$, $N_2$, N, $NH_3$, CO, O, $O_3$, $NO_2$, $N_2O$, NO, $H_2O$, OH, H, $H_2$, He, Ar, and Ne.

In one embodiment of the invention, schematically illustrated in FIG. 2, the sampling unit 11 is made in polydimethylsiloxande (PDMS), silicone, capton, rubber or other soft material with a Young's modulus of less than $10^5$ kPa. This makes it flexible enough to be attached to other parts of the body than the torso such as the head or the extremities of a neonate. In order to not hinder the functionality of certain parts of the sampling unit, such as the ambient air inlet 17 and the blood gas extraction and mixing cavity 19, the material may not be to flexible. A minimum Young's modulus to achieve the needed structural stability of these parts is 10 kPa. The above mentioned materials typically have Young's modulus in this range. It is also possible to combine materials to achieve the combination of flexibility and structural stability.

In one embodiment of the invention, the pressure in the blood gas extraction and mixing cavity 19 is reduced by making the flow resistance of the ambient air inlet 17 in the same order or larger than that of the combination of the outlet 18 and the tube 12. This can be achieved by making the cross section of the ambient air inlet 17 smaller than the cross section of the outlet 18 and/or the internal cross section of the tube 12. The reduced pressure creates an increased concentration gradient of $CO_2$ and $O_2$ across the skin surface, and, hence, and increased transcutaneous gas flux that improves the resolution and reduces the response time of the sensor unit 13. According to one embodiment the combination of the outlet 18 and the tube 12 has an 1-2 times lower flow resistance than the ambient air inlet 17 or the combined flow resistance of a plurality of ambient air inlets 17.

In further embodiments of the invention, the sensor unit 13 comprises several sensors that can measure the ambient amount of any of the species $CO_2$, $O_2$, $N_2$, Ar and $H_2O$. These sensors can be based on optical or electrochemical detection methods and are used to measure the ambient air quality. If the patient is treated in an incubator, these sensors can be installed inside the incubator and connected to the sensor unit 13 via an electrical interface. If the room or incubator where the patient is treated is equipped with air quality sensors to monitor the above stated gases, the output of these can be relayed to the sensor unit 13 via a data communication interface (not shown). Monitoring of the above stated gases can be used to continuously calibrate the sensor.

Figure 3:
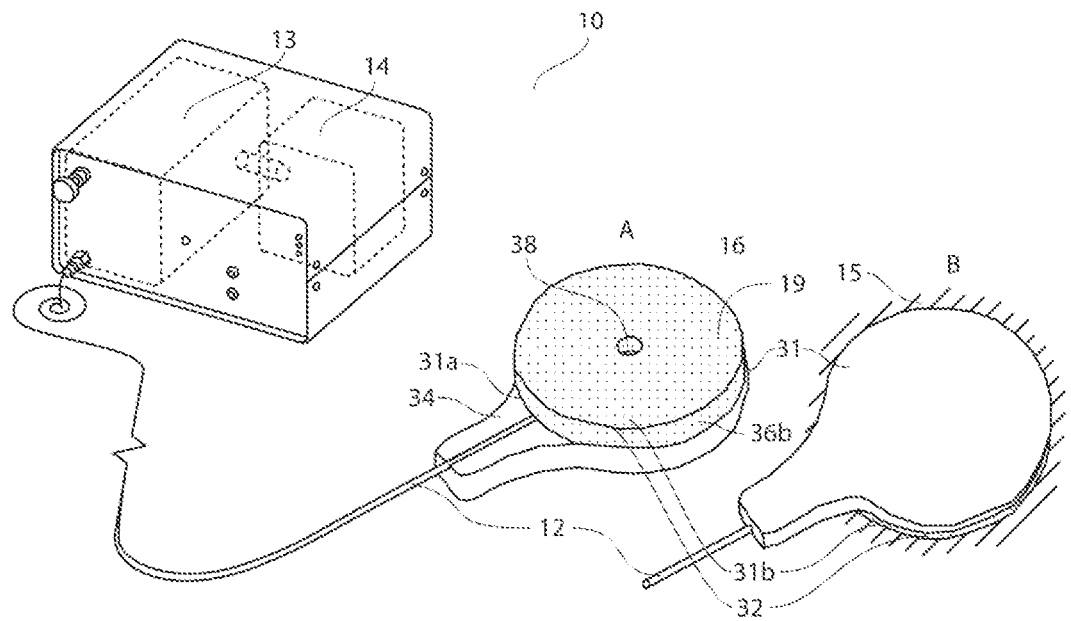
FIG. 3 is a schematic illustration of the sampling unit and TBM system according to one embodiment of the invention.

In one embodiment of the invention, schematically described in FIG. 3, the sampling unit 31 has an outlet 38 that is connected to the sensor unit through a tube 12. The sampling unit 31 is made in a gas permeable material 32, and has one skin facing side 31b facing the skin of a patient 15 and one ambient air facing side 36b facing the ambient air 16. The skin facing side 31b corresponds to the open side of the blood gas extraction and mixing cavity 19. The ambient air facing side 36b corresponds to the ambient air inlet 17, and bulk of the gas permeable material of the sampling unit 31 corresponds to the blood gas extraction and mixing cavity 19. The upper side 31a opposite of the skin facing side 31b of the sampling unit 31 is coated with a gas tight material 34. When the pump 14 is turned on, air enters the sampling unit 31 from the ambient air 16 through the gas permeable material 32 and flows to the outlet 38. This stabilizes the concentration gradient across the skin and, hence, keeps a stable transcutaneous gas flux.

In one embodiment of the invention, the tube 12 has a cross section between 0.0020 $mm^2$ and 0.031 $mm^2$, preferably between 0.0028 $mm^2$ and 0.0079 $mm^2$. This enables keeping the pressure in the sampling unit at atmospheric levels and the pressure in the sensor unit below 40 kPa.

In one embodiment of the invention the sensor unit 13 can measure the amount of $N_2$ and/or Ar in the gas coming from the sampling unit 11. By measuring these gases in addition to $CO_2$ and $O_2$, the sensor can detect leaks.

Figure 4:
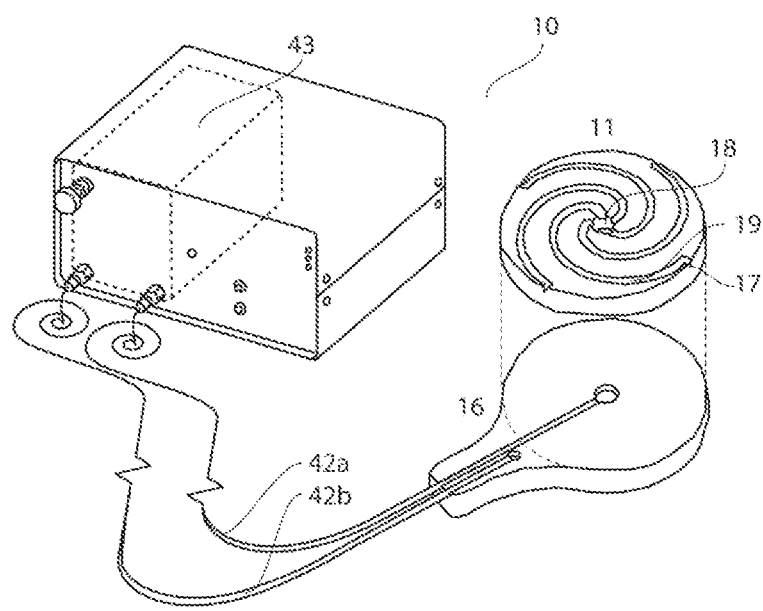
FIG. 4 is a schematic illustration of the TBM system according to one embodiment of the invention.

In one embodiment of the invention, schematically described in FIG. 4, a two-input sensor unit 43 is connected to a sampling unit 11 with two tubes, where the first tube 42a is connected to the part of the sampling unit 11 that collects the blood gases at the patient's skin 15, and the second 42b is collecting ambient air 16 from a place close to the sampling unit 11 but away from the patient's skin 15. The two-input sensor unit 43 contains a valve that can toggle between these two tube inputs, where the atmospheric sample can be used to continuously calibrate the sensor.

Figure 5:
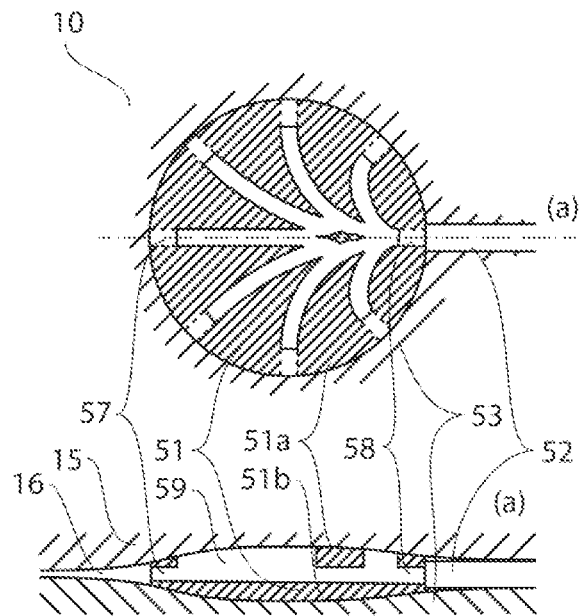
FIG. 5 is a schematic illustration of the sampling unit according to one embodiment of the invention.

In one embodiment of the invention, schematically described in FIG. 5, a non-adhesive sampling unit 51 that does not contain any glue or other adhesive to attach it to the skin of the patient 15 is used. Instead, the non-adhesive sampling unit 51 and tube 52 is made thin and soft so that the patient can lie on it without receiving any pressure damage. The sampling unit 51 has an upper side 51a and a lower side Sib without any attachment so that essentially flat surfaces are provided towards the skin 15 and an underlying surface 53 mattress, for example. The ambient air inlets 57 and the outlet 58 are provided on side surfaces of the sampling unit 51. Thereby, the tube 52, connecting to the outlet 58 extends in a direction parallel to the skin surface. In this way, the non-adhesive sample unit 51 is during use wedged between the patient's skin 15 and a the underlying surface 53, which creates a secure connection to the skin with respect to the ambient air 16, without the use of adhesives. According to one embodiment the ambient air inlets 57 are open to the skin and extended over the upper side 51a facing the skin and connected to the outlet 58. Thereby a combined ambient air inlet 57 and blood gas extraction and mixing cavity 59 is formed.

Heating is used in TBM in order to increase the capillary blood flow by causing vasodilation, i.e. widening of the cutaneous capillaries. When the capillaries dilate, the blood flow through them multiplies, making the fraction of arterial blood in the cutaneous capillaries increase rapidly, which enables measurement of the arterial $O_2$ pressure. Although vasodilation is the body's natural way of cooling, it is not directly caused by an increased temperature, but by signaling from the nervous system. In the case of local heating, temperature sensitive small nerve fibers close to the skin mediate local axon reflex-related vasodilation, creating a local increase in the capillary blood flow, i.e. the physical effect that makes arterial $O_2$ measurements feasible. Hence, it is not the continuous heating that is important, but rather the continuous stimulation of the small nerve fibers close to the skin.

Vasodilation and contraction is a rather slow process. Once the capillaries have been stimulated by the small nerve fibers, they dilate in the matter of seconds but it takes several minutes before they contract back to their original cross section. In other words, the relationship between skin temperature and blood flow is hysteretic, where a short nerve stimuli can result in a long period of increased blood flow in the cutaneous capillaries. [4]

Figure 6:
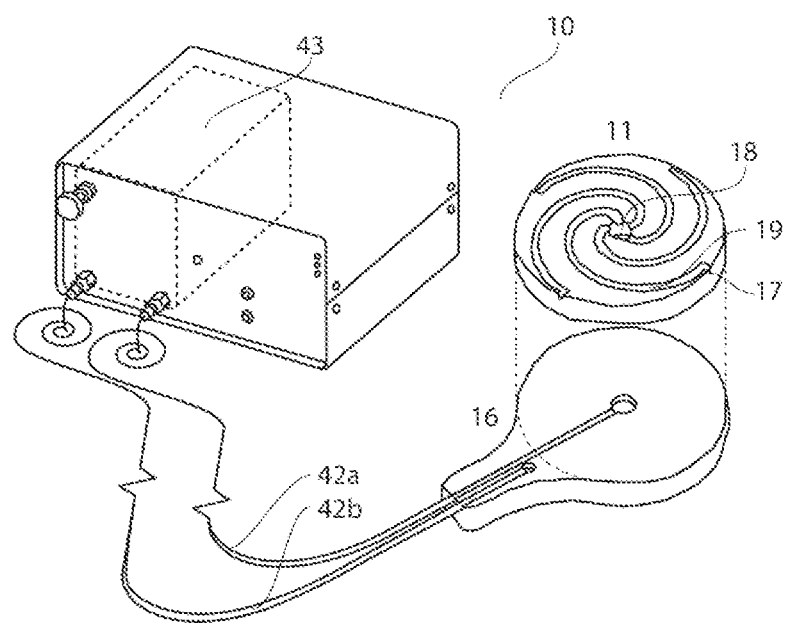
FIG. 6 is a schematic illustration of the sampling unit and TBM system according to one embodiment of the invention.

In further embodiments of the invention, illustrated in FIG. 6, the sampling unit 11 is equipped with a nerve stimulating element 61 capable of stimulating an axon reflex in small nerve fibers close to the skin. This element is connected to a signal generator 62 feeding it with a continuous pulsed signal. Pulse-width modulation is a method of reducing the average power of a signal by fractionating it into parts. When the element is powered with a continuous pulsed signal it transmit a continuous series of stimulation pulses into the skin of the patient 15, that activates the small nerve fibers close to the skin and, hence, causes axon reflex mediated vasodilation which enables measurement of the arterial blood gas pressure. By repeatedly transmitting stimulation pulses into the skin of the patient 15, the capillaries can be kept in the dilated state and the arterial blood gases can be monitored for longer times or even continuously.

In one embodiment of the invention, the nerve stimulating element 61 has the form of a heater that heats at least a portion of the surface of the skin beneath the sampling unit Other examples of nerve stimulating elements include an electrode that can stimulate the small nerve fibers electrically.

In one embodiment of the invention, the nerve stimulating element 61 can be used as an ECG electrode while in its unpowered state. In the unpowered state, the TBM system monitors the capillary blood gas levels simultaneously as the electrical connection to the electrode is switched to an ECG device (not shown) that monitors the patient's heart. When there is a need to measure the arterial blood gas levels, the electrode is switched back to the signal generator 62 of the TBM system.

Figure 7A:
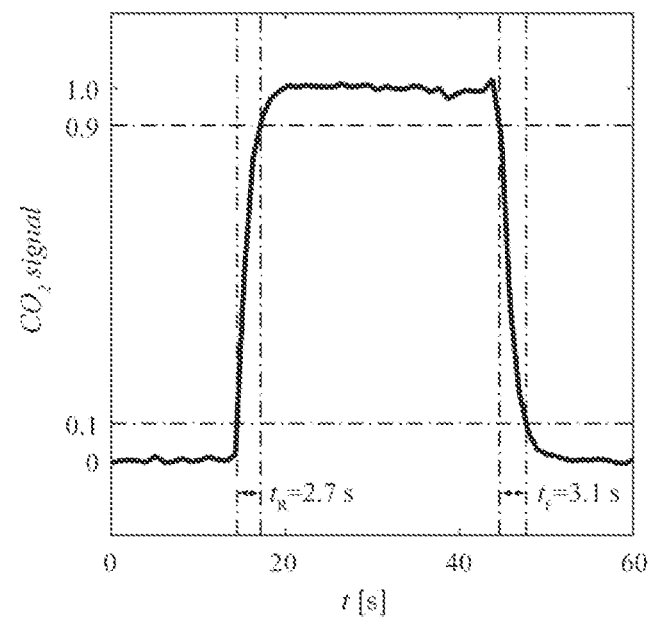
FIG. 7 a) and b) are graphs showing $CO_2$ signal as a function of time in contact with a TBM system of the invention.

FIG. 7a shows a graph of the measured $CO_2$ concentration as a system according to FIG. 1 was attached to a gas reservoir containing a calibrated gas mix of 20% $CO_2$ in air, at room temperature and atmospheric pressure. Hence, upon attachment and detachment the analyzed $CO_2$ concentration went from <0.1% to 20% and back to <0.1% again. The response time of the system was calculated from the rise time, $t_R$, and the fall time, $t_F$, of the signal by measuring the time required for the $CO_2$ signal to go from 10% to 90% of its final value, and vice versa, as indicated by the dash-dotted lines. The average response time, $(t_R+t_F)/2$, was about 3 s. This should be compared to the response times reported in Table IV of the cited prior art WO 2016/173877 that discloses response times between 36 s and 59 s, or the 2 minute measurement interval disclosed in the cited prior art U.S. Pat. No. 9,538,944B2. Hence, a system according to the invention can achieve more than 10 times faster analysis.

Figure 7B:
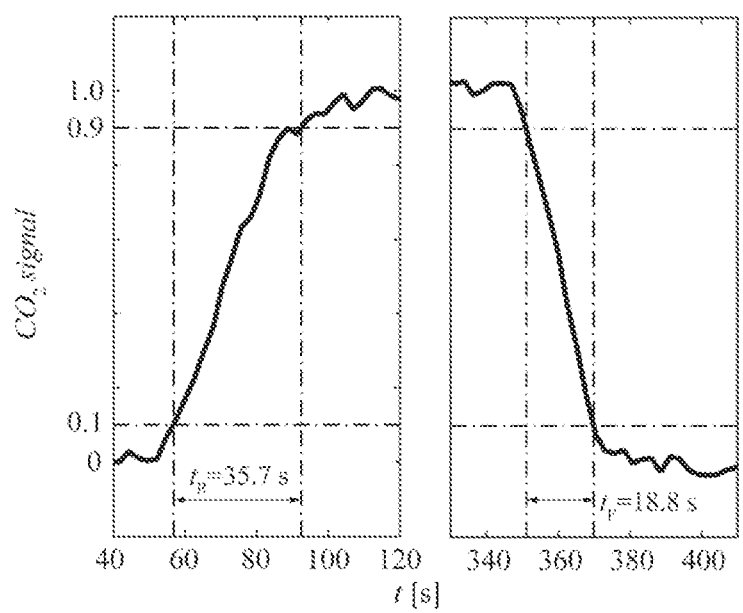

FIG. 7b shows a graph of the measured $CO_2$ concentration as a system according to FIG. 1 was attached to the unheated skin of an adult subject's arm. The rise and fall times where calculated resulting in an average response time of 27.3 s. This should be compared to response times of more than 10 minutes affiliated with commercially available instruments, e.g., SenTec's OxiVenT™ or Radiometer's TCMS.

Figure 8:
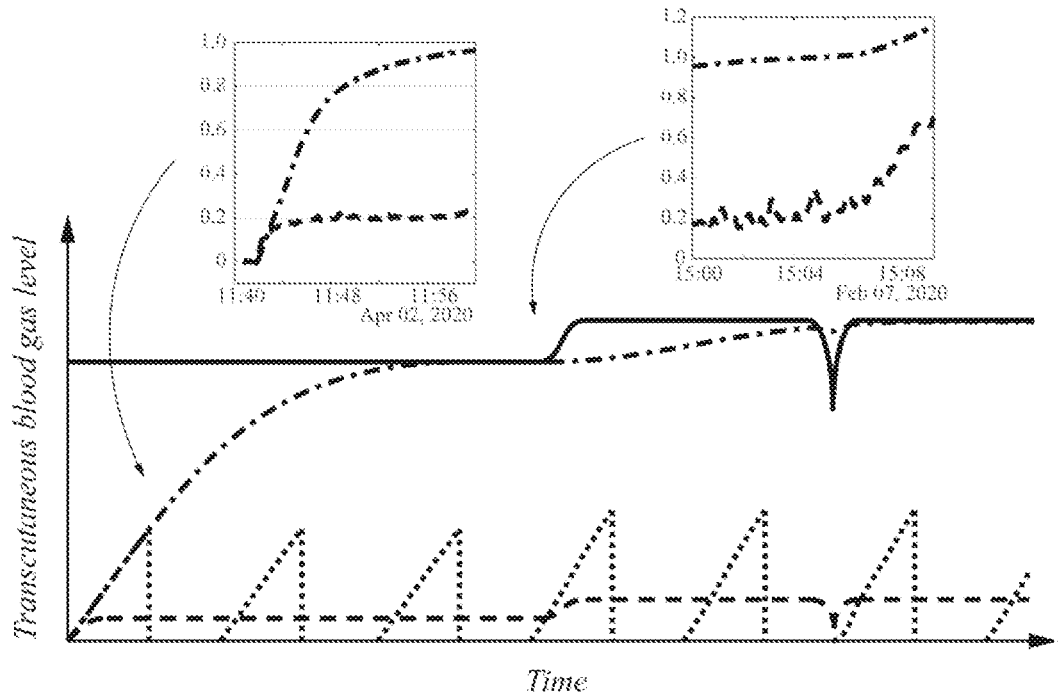
FIG. 8 is a graph comparing prior art measuring methods and the method according to the invention.

FIG. 8 shows an illustration of the response of different TBM systems to a change in a patient's blood gas level (solid line). Here, the dashed line corresponds to the response of a TBM system according to the invention, the dash-dotted line to a prior art TBM system relying on saturation of a closed system, e.g., the TBM system disclosed in the cited prior art WO 2016/173877, and the dotted line to a prior art TBM system relying on diffusion in a closed system, e.g., the TMB system disclosed in the cited prior art U.S. Pat. No. 9,538,944B2. As can be seen, both the initiation time at the start of the monitoring and the response to changes in patient's blood gas level is greatly improved over prior art. The lower gas level to be detected with the TBM system according to the invention does not constitute a problem using appropriate and described sensor units, such as the sensor unit comprising a stripline split-ring resonator microplasma source. It is an advantage of the present invention, i.e. a flow-based system, that it is able to monitor both fast and slow changes accurately, while a closed system relying on saturation cannot detect rapid events, and a closed system relying on diffusion risks missing them due to the required purging intervals during which measurements are not possible.

Embodiments of the sampling unit 11; 31; 51 comprising a nerve stimulating element 61 is suitable for a system and method according to the invention for continuous TBM that does not require continuous heating of the patient's skin, referred to as the continuous pulsed signal method and system.

Heating is used in TBM in order to increase the capillary blood flow by causing vasodilation of the cutaneous capillaries. Although vasodilation is the body's natural way of cooling, it is not directly caused by an increased temperature, but by signaling from the nervous system. In the case of local heating, temperature sensitive small nerve fibers close to the skin mediate axon reflex-related vasodilation, creating a local increase in the capillary blood flow, i.e. the physical effect that makes TBM feasible.

With reference to the description referring to FIGS. 1 and 6 the TBM system 10 is further provided with a signal generator that is connected to a control unit. The sensor unit 13 is configured to at least measure $CO_2$ and $O_2$ in the extracted blood gas. The TBM system 10 may further be provided with an input/output device as well as communication unit for remote control and/or supervision. The results from the measurement are typically displayed on a display monitor. The display monitor is preferably continuously updated to show real-time data of the patient's blood gas status.

The nerve stimulating element 61 is any element capable of stimulating a local axon reflex in small nerve fibers close to the skin underneath the sampling unit 11; 31; 51. In one embodiment of the invention the nerve stimulating element 61 is a heater that heats at least a portion of the skin surface covered by and underneath the sampling unit 11; 31; 51. Due to the continuous pulsed signal transmitted by the TBM system 10 the heating is not continuous but pulsed, and hence the risk of skin burns is reduced, since the skin 15 has time to recover between the pulses. The heater may for example be a resistive heater, a thermoelectric heater or an IR-heater and the generated pulse an electrical pulse with a current/voltage that matches the characteristics of the resistive heater. Suitable resistive or thermoelectric heaters are commercially available, e.g., Miniature Flex-Coils from MINCO, but preferably the heating element may be custom made to fit a specific sampling unit 11; 31; 51. The nerve stimulating element 61 may alternatively be an electrode that stimulates the small nerve fibers electrically or any other suitable stimulation element.

The TBM system 10 is adapted to transmit a continuous pulsed signal, i.e. a continuous series of stimulating pulses, to the skin 15 inducing a local axon reflex in small nerve fibers located underneath the sampling unit 11; 31; 51. The signal generator is configured to generate a continuous pulsed signal, for example and typically electrical pulses which by the nerve stimulating element 61 are transmitted to the skin of the patient as a continuous series of pulses, hereinafter referred to as stimulation pulses. The local axon reflex induced by the stimulation pulses induces vasodilation which enables the blood gas measurement.

Figure 9:
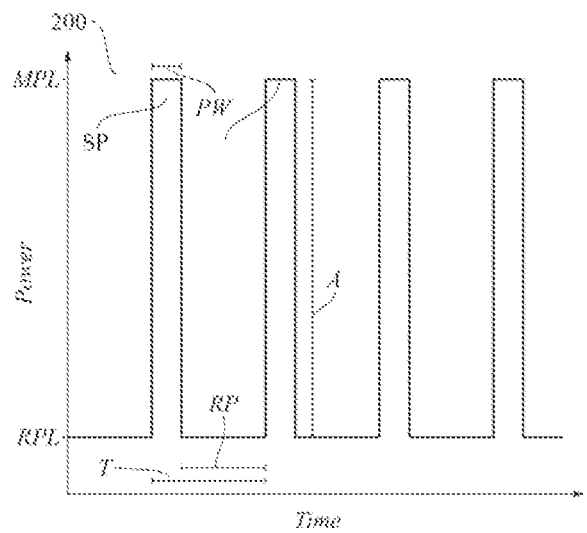
FIG. 9 is a schematic illustration of a continuous pulsed signal according to the method of the invention.

The continuous pulsed signal can be described by a pulse-scheme 200, which is schematically illustrated in FIG. 9, and comprises stimulation pulses SP and relaxation periods, RP. The stimulation pulse SP has a maximum power level, MPL, and a pulse width, PW, the relaxation periods, RP, has a power level, the relaxation power level, RPL. The amplitude, A, is the difference between the maximum power level, MPL, for the stimulation pulse SP and the power level, RPL, for the relaxation period RP. The area under the curve of a stimulation pulse SP represents the submitted energy to the skin during one simulation pulse. The shape of the simulation pulses are illustrated as essentially rectangular, which represents typical stimulation pulses SP. As realized by the skilled person other shapes of the stimulation pulses SP are possible and ramping up and/or down the power in a predetermined manner may be advantageous or required for certain heaters, for example. The maximum power level, MPL, of the stimulation pulse SP and its pulse width, PW, should be chosen to correspond to a heating of the skin underneath the sampling unit 11; 31; 51 of the TBM system 10 to a temperature of 42 to 45° C. The relaxation power level, RPL, should be selected to give an effective relaxation, typically cooling down. According to one embodiment the relaxation power level, RPL, is zero.

A common way to describe a pulsed signal is with the parameter duty cycle, D, defined as $$D = PW/T \qquad [1]$$

Wherein PW is the pulse width of the stimulation pulse SP and T is the period, i.e. the pulse width PW of the stimulation pulse added with the relaxation period RP.

The method for transcutaneous blood gas measurement according to the invention enables continuous measurement of the blood gases (oxygen and carbon dioxide) without continuous heating of the patient's skin 15. The method utilizes a TBM system 10 comprising a nerve stimulating element 61 and a pulse generator. The pulse generator transmits a continuous pulsed signal 200 to the nerve stimulating element 61 that transmits a continuous series of stimulation pulses SP to the skin 15. The continuous series of stimulation pulses SP induces vasodilation in the cutaneous capillaries affected by the nerve stimulating element 61.

The TBM method according to the invention comprises the main concurrent steps of:
a) continuously transmitting a continuous pulsed signal 200 to the nerve stimulating element 61 that transmits a continuous series of stimulation pulses to the skin 15 of the patient, thereby inducing vasodilation in the cutaneous capillaries located in the interface with the sampling unit 11; 31; 51 and maintaining the vasodilation in the cutaneous capillaries in order to achieve a continuous transcutaneous blood gas flux;
b) continuously extracting the transcutaneous blood gas from the patient into the TBM system 10;
c) continuously measuring the oxygen concentration and/or the carbon dioxide in the extracted transcutaneous blood gas with an oxygen sensor and/or a carbon dioxide sensor in the sensor unit 13; and
d) continuously analyzing the signals from the oxygen sensor and/or a carbon dioxide sensor and determining oxygen and/or and carbon dioxide levels in the extracted transcutaneous blood gas and continuously presenting the results, for example on a display monitor.

In order for the TBM system 10 to provide the continuous measurement the vasodilation needs to be above a threshold value, referred to as the vasodilation threshold value, VTV. This vasodilation threshold value, VTV, corresponds to a capillary cross section that is sufficiently wide to allow enough arterial blood to enter the cutaneous capillaries for the arterial blood gas levels to dominate the measured signal. A suitable maximum power level, MPL, of the stimulation pulse SP giving a vasodilation above the vasodilation threshold value, VTV, will depend on the specific configuration of the TBM system 10 and may without undue burden be determined by a person skilled in the art. For example, in the embodiment using a heater as the nerve stimulating element the designer given the instructions that the maximum power level, MPL, should correspond to a maximum temperature of the skin of 42-45° C., would establish appropriate parameters for the heater with only a few tests.

An exemplary suitable pulse scheme is schematically illustrated in FIG. 10a by a graph that shows a continuous pulsed signal that corresponds to a method according to the invention. The pulse width is 2 s and the subsequent relaxation time is 118 s. FIG. 10b shows the calculated relative blood flow and fraction of arterial blood gas in the cutaneous capillaries arising from the axon stimuli that occurs when the signal in FIG. 10a feeds the nerve stimulating element 61, which in this case is a heater that heated the skin to 43° C. The left y-axis shows relative blood flow (dashed and dotted lines) where 1 corresponded to the blood flow in the undilated (unstimulated) capillaries, and the right y-axis shows the fraction of arterial blood gas in the cutaneous capillaries (solid and dash-dotted lines). Of these lines, the solid and dashed ones show the situation when the method according to the invention is employed, resulting in a significantly increased cutaneous blood flow, as well as a high and stable fraction of arterial blood gas in the capillaries. The dotted and dash-dotted lines, on the other hand, show the situation when the skin is only subjected to the initial 40 s of heat but none of the subsequent pulses. In the latter case, or when the continuous pulsed signal is discontinued, the cutaneous capillaries contract back to their original cross-section after a time period of typically 300-600 s. An example of a vasodilation threshold value VTV is shown by the thin solid line.

Figure 11A:
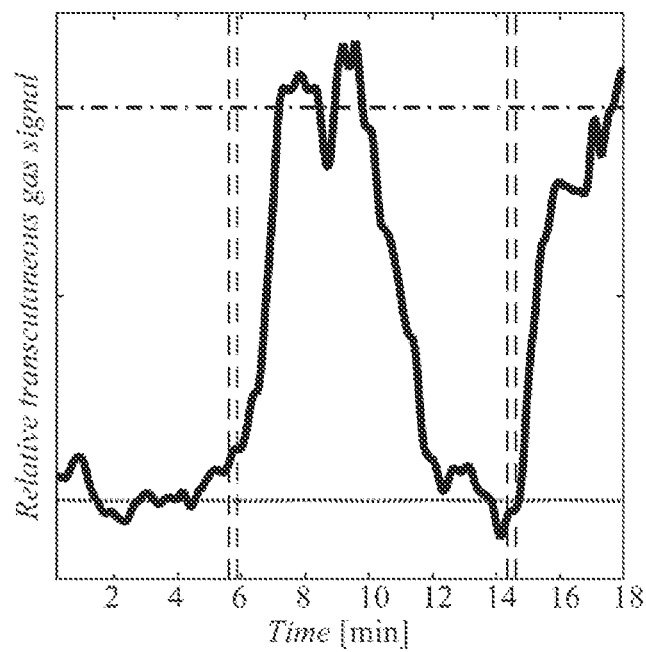
FIG. 11 a) is a graph showing relative transcutaneous gas signal as a function of time, and b) is a graph showing relative transcutaneous gas signal as a function of time.

FIG. 11a is a graph of a measurement of relative transcutaneous gas signal as a function of time using a TBM system 10 described with reference to FIG. 1 with a thermoelectric heater. From t=0 the TBM system 10 is monitoring the capillary blood gas level, indicated by the dotted line. At t=6.5 minutes, the heater is activated with a continuous pulsed signal 200 that comprises a series of stimulation pulses SP with a maximum power level, MPL, corresponding to a temperature of 45° C. The stimulation pulses SP each have a pulse length, PW, of 15 s and the following relaxation periods, RP, each are 465 s long, making up a total period, T, of 480 s and duty cycle, D, of 3.1%. The relaxation power level, RPL, was 0 W. The timing of the pulses is indicated by vertical dashed lines in the graph. Directly after a stimulation pulse SP, the signal rises to the arterial level, indicated by the dash-dotted line, and remains there for about 180 s. It then relaxes back to the capillary level, before being raised again by the second pulse.

Figure 11B:
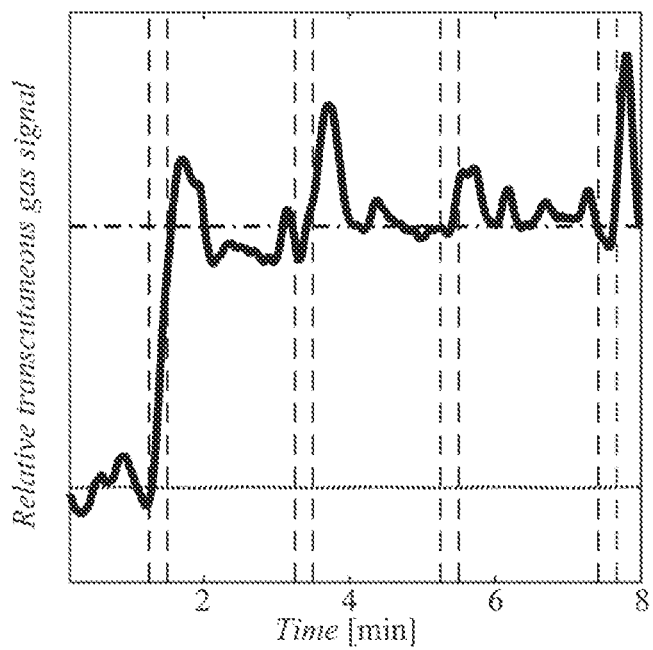

FIG. 11b illustrates a measurement with the same equipment as in FIG. 10a and is a graph of a relative transcutaneous gas signal as a function of time for a continuous pulsed signal 200 with a shorter period, T. Here, the continuous pulsed signal 200 has the same maximum power level MPL (45° C.) and pulse length, PW, (15 s) as in FIG. 10a, but the relaxation periods, RP, each are 105 seconds long, making up a total period, T, of 120 s and duty cycle, D, of 12.5%. The first stimulation pulse SP of the continuous pulsed signal 200 raises the signal from the capillary blood gas level (dotted line) to the arterial blood gas level (dash-dotted line) and the following pulses keeps the signal at the latter, hence, enabling continuous monitoring of arterial blood gases without continuous heating. FIG. 11b illustrates that the method according to the invention facilitates the continuous measurements without continuous heating.

In the process of continuously transmitting a continuous pulsed signal to the nerve stimulating element 61, during the stimulation pulse SP the nerves are stimulated so that the local axon reflex induces vasodilation to a sufficient degree that enables the measurement of the oxygen concentration and/or the carbon dioxide concentration in the extracted gas. According to one embodiment vasodilation is induced by applying heat and the stimulation pulse SP comprises applying heat in an amount so that the temperature of the skin during the stimulation pulse SP rises to in-between 42 and 45° C. During the relaxation period, RP, the applied amount of heat is lowered or completely turned off so that the temperature of the skin is lowered to the temperature of the skin prior to receiving the first stimulation pulse SP.

The requirements regarding measurability of the carbon dioxide concentration in the extracted gas without risk for erythema is fulfilled for a continuous pulsed signal with a maximum power level, MPL, corresponding to a maximum temperature of the skin of 42-45° C. and the nerve stimulating pulses SP having a pulse width, PW, between 2 and 180 s and the relaxation period, RP, being between 105 and 180 s, which corresponds to one embodiment of the invention. This corresponds to a duty cycle, D, of at the most 50%.

According to one embodiment of the invention the system and method is optimized for providing high accuracy, by increasing the vasodilation threshold value, VTV, hence, keeping the arterial blood gas fraction in the cutaneous capillaries at a higher and steadier fraction, however, still complying with the requirements of the heating. According to this embodiment the continuous pulsed signal has a maximum power level, MPL, corresponding to a maximum temperature of the skin of 42-45° C. and the nerve stimulating pulses SP has a pulse width, PW, between 2 and 15 s and the relaxation period, RP, is between 105 and 118 s. This corresponds to a duty cycle, D, of at the most 13%.

According to one embodiment of the invention the system and method is optimized for minimizing the heating effect further by minimizing the pulse width, PW, which could be used for extremely sensitive patients. In this case the accuracy of the measurement may be lower, however acceptable in most monitoring situations. According to this embodiment the continuous pulsed signal has a maximum power level, MPL, corresponding to a maximum temperature of the skin of 42-45° C. and the nerve stimulating pulses SP has a pulse width, PW, between 2 and 8 s and the relaxation period, RP, is between 120 and 180 s. This corresponds to a duty cycle, D, of at most 6%.

The embodiments described above are to be understood as illustrative examples of the system and method of the present invention. It will be understood that those skilled in the art that various modifications, combinations and changes may be made to the embodiments. In particular, different part solutions in the different embodiments can be combined in other configurations, where technically possible.

REFERENCES

[1] I. Bromley, "Transcutaneous monitoring—understanding the principles", Infant, vol. 4, p. 95-98, 2008.
[2] "Transcutaneous Blood Gas Monitor", http://www.who.int/medical_devices/en/index.html, World Health Organization.
[3] D. Lübbers, "Theoretical basis of the transcutaneous blood gas measurement", Critical Care Medicine, vol. 9, 1981.
[4] W. Mager land R. D. Treede, Heat-evoked vasodilatation in human hairy skin: axon reflexes due to low-level activity of nociceptive afferents. Journal of Physiology, 497.3, pp. 837-848, 1996.

The invention claimed is:

1. A sampling unit to be used in a system for transcutaneous blood gas measurement, comprising:
   a sensor unit, a tube and a pump, the pump enabling a gas flow into the sampling unit through the tube and to the sensor unit, the sensor unit configured to measure a gas composition of the gas flow, the sampling unit configured to during use be attached to the skin of a patient,
   wherein the sampling unit is characterized by:
   at least one blood gas extraction and mixing cavity in fluid connection with an ambient air inlet and in fluid connection with an outlet configured to be connected to the tube, the at least one blood gas extraction and mixing cavity provided on the side of the sampling unit facing the skin;

at least one ambient air inlet; wherein the ambient air inlet is arranged to continuously provide ambient air to the at least one blood gas extraction and mixing cavity; and wherein the combination of the outlet and the tube has an 1-2 times lower flow resistance than the at least one ambient air inlet or the combined flow resistance of a plurality of such ambient air inlets.

2. The sampling unit according to claim 1, wherein the sampling unit is made in a material with a Young's modulus of less than $10^5$ kPa.

3. The sampling unit according to claim 2, wherein the sampling unit is made in one of the materials or a combination of polydimethylsiloxande, silicone, capton, and rubber.

4. The sampling unit according to claim 1, wherein a cross-section of the outlet and/or an internal cross-section of the tube is larger than a cross-section of the at least one ambient air inlet or the combined cross section of a plurality of such ambient air inlets.

5. The sampling unit according to claim 4, wherein the cross-section of the outlet and/or the internal cross-section of the tube is 0.0020 mm²–0.031 mm².

6. The sampling unit according to claim 4, wherein the cross-section of the outlet is 0.0028 mm²–0.0079 mm².

7. The sampling unit according to claim 4, wherein the internal cross-section of the tube 0.0028 mm²–0.0079 mm².

8. The sampling unit according to claim 1, wherein at least a portion of the sampling unit is made in a gas permeable material that serves as a blood gas extraction and mixing cavity and has one skin facing side facing the skin and one ambient air facing side in fluid connection with the ambient air.

9. The sampling unit according to claim 8, wherein the combination of the outlet and the tube has a flow resistance at or less than that of air entering the sampling unit through ambient air facing side passing through the gas permeable material and exiting to the outlet.

10. The sampling unit according to claim 1, further comprising a nerve stimulating element configured to stimulate an axon reflex in small nerve fibers close to the skin.

11. The sampling unit according to claim 10, wherein the nerve stimulating element is a heater.

12. The sampling unit according to claim 11, wherein the nerve stimulating element is a combined heater and ECG electrode.

13. A system for transcutaneous blood gas measurement for measurement of carbon dioxide, comprising:
a sampling unit including:
a sensor unit,
a tube, and
a pump configured to enable a gas flow into and through the sampling unit and through the tube into and through the sensor unit,
wherein the sensor unit is configured to measure a gas composition of the gas flow,
wherein the sampling unit is configured to during use be attached to the skin of a patient,
wherein the sampling unit is characterized by:
at least one blood gas extraction and mixing cavity in fluid connection with an ambient air inlet and in fluid connection with an outlet configured to be connected to the tube, the at least one blood gas extraction and mixing cavity provided on the side of the sampling unit facing the skin, and
at least one ambient air inlet; wherein the ambient air inlet is arranged to continuously provide ambient air to the at least one blood gas extraction and mixing cavity, and wherein the combination of the outlet and the tube has an 1-2 times lower flow resistance than the at least one ambient air inlet or the combined flow resistance of a plurality of such ambient air inlets.

14. The system for transcutaneous blood gas measurement according to claim 13, wherein the sensor unit comprises a microplasma source having an internal volume of at or less than 100 mm³ and an operating pressure of at or less than 40 kPa.

15. The system for transcutaneous blood gas measurement according to claim 14, wherein the microplasma source is a stripline split-ring resonator microplasma source.

16. The system for transcutaneous blood gas measurement according to claim 13, wherein the sensor unit comprises several sensors to measure different gases.

17. The system for transcutaneous blood gas measurement according to claim 13, wherein the sensor unit is configured to detect the amount of $N_2$ and/or Ar in the gas coming from the sampling unit.

18. The system for transcutaneous blood gas measurement according to claim 13, wherein the sensor unit is a two-tube sensor unit, that is connected to the sampling unit with two tubes, wherein the first tube is connected to the outlet, and the second is collecting ambient air from a place close to sampling unit but away from the skin.

19. The system for transcutaneous blood gas measurement according to claim 18, wherein the two-tube sensor unit is configured to toggle between the two tube inputs.

* * * * *